United States Patent [19]

Vroman

[11] Patent Number: 5,330,653
[45] Date of Patent: Jul. 19, 1994

[54] METHOD FOR THE REDUCTION OF HYDROGEN SULFIDE IN SEWAGE TREATMENT PLANTS

[75] Inventor: Albert L. Vroman, Portland, Mich.

[73] Assignee: Zing Odor Control, Inc., Portland, Mich.

[21] Appl. No.: 75,789

[22] Filed: Jun. 14, 1993

[51] Int. Cl.$^5$ ............................ C02F 3/00; A61L 11/00
[52] U.S. Cl. ........................................ 210/631; 422/5; 424/76.5; 424/76.6; 424/76.7
[58] Field of Search .................. 422/5; 424/76.5–76.7, 424/21; 210/631; 514/532

[56] References Cited

U.S. PATENT DOCUMENTS

| 1,410,249 | 3/1922 | Henderson et al. | 424/76.5 |
| 3,113,104 | 12/1963 | Bersworth | 424/76.6 |

FOREIGN PATENT DOCUMENTS

| 357 | 1/1987 | Japan | 424/76.6 |
| 292962 | 11/1988 | Japan | 424/76.5 |
| 317441 | 12/1989 | Japan | 424/76.5 |
| 111054 | 5/1991 | Japan | 424/76.6 |

OTHER PUBLICATIONS

Hercules Chemcial Company, Inc., "WHAM" Product Information Sheet, 1984.
Kirk Othmer 24, 407–418 (1984).

*Primary Examiner*—Neil McCarthy
*Attorney, Agent, or Firm*—Ian C. McLeod

[57] ABSTRACT

A method for the reduction of hydrogen sulfide in an enclosure which is involved in processing sewage and where workmen are present wherein methyl benzoate is used an additive to the sewage is described. The methyl benzoate is preferably in the form of a dilute aqueous emulsion. The emulsifier is preferably a polyoxyethylene derivative of a sorbitan fatty acid ester and most preferably, polyoxyethylene (20) sorbitan monolaurate.

12 Claims, No Drawings

METHOD FOR THE REDUCTION OF HYDROGEN SULFIDE IN SEWAGE TREATMENT PLANTS

BACKGROUND OF THE INVENTION

1. Field of The Invention

The present invention relates to the use of methyl benzoate as an additive to sewage to reduce the generation of hydrogen sulfide in an enclosure where humans may be exposed to the hydrogen sulfide. In particular, the present invention relates to the use of methyl benzoate in a dilute aqueous emulsion as an additive to the sewage.

2. Description of Related Art

Methyl benzoate is sold commercially under the trademark ZING by Zing Agricultural Product Applications, Inc., Portland, Mich., as an aqueous emulsion for odor control in sewage and livestock manure. The emulsifier is a small volume of a non-toxic soap or detergent which allows the methyl benzoate to be mixed with water. This product is also used to dissolve and control grease, sludge, soap and detergent deposits, particularly in drains and sink traps. It is approved under EPA regulations and is considered safe for use in the environment.

The municipal treatment of raw sewage to separate water and a sludge is well known to those skilled in the art. It is described in detail in Kirk Othmer 24 407 to 418 (1984) and in numerous other publications on the subject. The process generally involves sewage pumping, settling and biological treatment in various forms. In general, the process equipment is housed in an enclosure in which humans at least periodically have to work.

Hydrogen sulfide is generated from sewage in amounts which are dangerous to humans and which can be fatal. The method of the prior art method for removing hydrogen sulfide is to vent the gas to the atmosphere. The smell is unpleasant (rotten egg odor) and persons around the enclosure, particularly downwind, can become sick with headaches, rashes and the like. Since hydrogen sulfide is an acid, it is corrosive to equipment. There is a need for the reduction of the hydrogen sulfide generated by the sewage.

Hydrogen sulfide gas is a dangerous problem in sewage treatment plants. Under OSHA rules in the U.S. (29 CFR 1910.1000), the time weighted average (TWA) for an employee in an eight hour shift for a 40 hour work week for hydrogen sulfide is 10 ppm (14 rag/m$^3$). The short term exposure limit (STEL) at any time during a work week is 15 ppm (21 mg/m$^3$). As can be seen, hydrogen sulfide is quite poisonous and presents a significant health risk for workmen.

OBJECTS

It is therefore an object of the present invention to provide a novel method and compositions for treating the sewage to very significantly reduce the generation of hydrogen sulfide in enclosures in which humans must work. Further, it is an object to provide a method which is simple and economical. These and other objects will become increasingly apparent by reference to the following description.

DESCRIPTION OF PREFERRED EMBODIMENTS

The present invention relates to a method for reducing hydrogen sulfide in an enclosure housing equipment in which sewage is to be processed and in which humans at least periodically work which comprises: admixing methyl benzoate in the sewage in an amount which reduces the hydrogen sulfide in the enclosure. The enclosure can be a sewage pumping substation or a sewage treatment plant for instance. A composition including the methyl benzoate in an amount between about 1 to 10% by volume and about three-tenths (0.3) or less of this amount of an emulsifier is preferably added in an amount between about $0.01 \times 10^{-3}$ to $0.5 \times 10^{-3}$ part per part by volume of the sewage.

Further, the present invention relates to a method for reducing hydrogen sulfide in a sewage treatment plant including an influent of sewage into the plant settling tank, means for microbial treatment of the sewage after the settling tank and a liquid effluent and a treated sewage which are removed from the plant which comprises adding an amount of a composition which is an aqueous emulsion of methyl benzoate to the sewage so as to reduce the hydrogen sulfide in the plant. The aqueous emulsion of the methyl benzoate can be added in the influent to the plant, settling tank(s) or it can be added to equipment for microbial treatment of the sewage to reduce the hydrogen sulfide.

Finally the present invention relates to a composition adapted for sewage treatment to reduce hydrogen sulfide when mixed with water which comprises: methyl benzoate; and a polyoxyethylene derivative of a sorbitan fatty acid ester, wherein the ratio by volume of (a) to (b) is between about 1 to 1 and 20 to 1, wherein the composition when added to sewage reduces hydrogen sulfide.

It is preferred to use an emulsifier with water and the methyl benzoate to provide a composition for treatment of the sewage. The most preferred emulsifiers are polyoxyethylene derivatives of sorbitan fatty acid esters which are non-ionic surfactants. Most preferred is TWEEN 20, which is polyoxyethylene 20/sorbitan monolaurate manufactured by ICI Americas, Inc., located in Spartanburg, S.C. This emulsifier has a hydrophile-lipophile balance (HLB) value of 16.9 out of 20 which means that it is hydrophilic. Preferably the range of HLB is between about 10 and 19.

The preferred aqueous compositions include

| (1) | Methyl benzoate | 9.6 oz (283.7 cc) |
|---|---|---|
| | TWEEN 20 emulsifier | 2 oz (59.14 cc) |
| | Water | 1 gallon (3.78 liters) |

With 116.4 oz (3.44 liters) of water then added per gallon subsequently

This provides about 3.9% methyl benzoate and 0.82% of the emulsifier in the finished composition, by volume.

| (2) | Methyl benzoate | 15 oz (443.5 cc) |
|---|---|---|
| | TWEEN 20 emulsifier | 2 oz (59.14 cc) |
| | Water | 1 gallon (3.78 liters) |

With 111.4 oz (3.28 liters) of water then added per gallon subsequently

This provides about 6.3% methyl benzoate and about 0.84% of the emulsifier in the finished composition, by volume.

| (3) | Methyl benzoate | 5 oz (147.6 liters) |
|---|---|---|
| | TWEEN 20 emulsifier | 1 oz (29.57 cc) |

| -continued | |
|---|---|
| Water | 1 gallon (3.78 liters) |

With 121 oz (3.57 liters) of water then added per gallon subsequently.

This provides about 2.0% of the methyl benzoate and about 0.4% emulsifier in the finished composition, by volume.

The concentrate, before further water is added, is produced in a large, closed vessel having a propeller mixer with the ingredients under pressure (1100 psig) for thirty (30) minutes. The water is then added to produce composition (1), (2) or (3). For sewage treatment it was found that composition (2) was preferred. The compositions are preferably added in a ratio to the sewage by volume of between about $0.05 \times 10^{-3}$ to $0.125 \times 10^{-3}$ part of the composition per part of the sewage.

The methyl benzoate is preferably used in a volume ratio to emulsifier of between about 1 to 1 and 20 to 1. The methyl benzoate is preferably used in water in a ratio between about 1 to 100 and 1 to 4.

EXAMPLE 1

Testing was conducted for hydrogen sulfide odors at a substation for a waste water treatment plant. The substation was a large underground sewage storage area that collected waste from the surrounding facilities and pumped it to the waste water treatment plant.

Before workmen could enter the substation, the building was opened up and fans were turned on to try to dissipate the hydrogen sulfide. A hydrogen sulfide gas testing gauge was used to check the air before entering. At first the meter read 160 ppm before entering. Federal law dictates a reading should be 7 ppm (400 ppm on the scale being deadly). The device initially read about 75 ppm upon entering. Composition (2) above was added to the waste in an amount of about $0.05 \times 10^{-3}$ part per part of the sewage by volume and the reading on the gas meter immediately dropped to 35 ppm. Within ten minutes of application and the gas meter was down to only 5 ppm. The methane gas and odors were also reduced.

EXAMPLE 2

The composition (2) was added to a tank (polymer tank) which directly feeds a thickener tank with a sewage settling polymer in a sewage treatment plant in an amount of about $0.05 \times 10^{-3}$ part per part of the sewage by volume. There was a significant reduction of hydrogen sulfide and odor in the tank and in belt presses which are used to remove the sludge from the tanks.

EXAMPLE 3

The composition (2) was added to a scum concentrator which is an overflow system for removing scum from settling tanks. The amount added was about $0.1 \times 10^{-3}$ part of the composition (2) per part of the sewage by volume. There was an elimination of the odor and gas concentrations immediately. It is forecast that the reduction in hydrogen sulfide will reduce equipment replacement costs because of corrosion from hydrogen sulfide.

The mechanism for the reduction of hydrogen sulfide by methyl benzoate is not understood. It is speculated that the microorganisms in the sewage may preferentially metabolize the methyl benzoate in a manner which does not generate hydrogen sulfide.

The foregoing description is only illustrative of the present invention and the present invention is limited only by the hereinafter appended claims.

We claim:

1. A method for reducing hydrogen sulfide in an atmosphere in an enclosure housing equipment in which sewage is process and in which humans at least periodically work which comprises:
    admixing methyl benzoate in the sewage in an amount of between about $0.05 \times 10^{-3}$ and $0.125 \times 10^{-3}$ part per volume of an aqueous composition containing 2.0 to 6.3% by volume methyl benzoate per part by volume of the sewage which amount reduces the hydrogen sulfide in the atmosphere in the enclosure to a level which does not exceed 15 ppm.

2. The method of claim 1 wherein the enclosure is around a sewage substation pump.

3. The method of claim 1 wherein the enclosure is around a sewage treatment plant.

4. A method for reducing hydrogen sulfide in an atmosphere in a sewage treatment plant including an influent of sewage into a settling tank for the sewage, means for microbial treatment of the sewage after the settling tank and a liquid effluent and a treated sewage which are removed from the plant which comprises adding an amount of a composition which is an aqueous emulsion of methyl benzoate to the sewage in an amount of between about $0.05 \times 10^{-3}$ and $0.125 \times 10^{-3}$ part per volume of an aqueous composition containing 2.0 to 6.3% by volume methyl benzoate per part by volume of the sewage which amount reduces the hydrogen sulfide in the atmosphere in the plant to a level which does not exceed 15 ppm.

5. The method of claim 4 wherein the methyl benzoate composition is added to the influent of the sewage which enters the plant.

6. The method of claim 4 wherein the methyl benzoate composition is added to the means for microbial treatment of the sewage.

7. The method of claim 4 wherein the methyl benzoate composition contains a plyoxyethylene sorbitan monolaurate as an emulsifier to provide the emulsion.

8. The method of claim 7 wherein the emulsifier is present in the composition in a ratio by volume to the methyl benzoate of between about 1 to 1 and 1 to 20.

9. The method of claim 7 wherein the emulsifier is polyoxyethylene (20) sorbitan monolaurate.

10. The method of claim 9 wherein the emulsifier is present in the composition in a ratio by volume to the methyl benzoate of between about 1 to 1 and 1 to 20.

11. The method of claim 1 wherein the composition contains an emulsifier for the methyl benzoate so as to provide an aqueous emulsion.

12. The method of claim 4 wherein the composition contains an emulsifier for the methyl benzoate so as to provide an aqueous emulsion.

* * * * *